(12) United States Patent
Greiner

(10) Patent No.: US 7,905,426 B1
(45) Date of Patent: Mar. 15, 2011

(54) FRAGRANCE EMITTING SNOW GLOBE

(75) Inventor: Lori Greiner, Chicago, IL (US)

(73) Assignee: For Your Ease Only, Inc., Chicago, IL (US)

( * ) Notice: Subject to any disclaimer, the term of this patent is extended or adjusted under 35 U.S.C. 154(b) by 283 days.

(21) Appl. No.: 12/120,579

(22) Filed: May 14, 2008

(51) Int. Cl.
*A61L 9/04* (2006.01)

(52) U.S. Cl. ............. 239/44; 40/406; 40/410; 422/123; 422/124

(58) Field of Classification Search ............... D23/367
See application file for complete search history.

(56) References Cited

U.S. PATENT DOCUMENTS

| | | | |
|---|---|---|---|
| 2,754,554 A * | 7/1956 | Mills .............................. | 422/121 |
| 4,961,276 A | 10/1990 | Lin | |
| 5,555,656 A | 9/1996 | Liu | |
| 5,567,361 A * | 10/1996 | Harper ............................ | 261/26 |
| 5,666,750 A | 9/1997 | Segan et al. | |
| 5,711,099 A | 1/1998 | Nesbit et al. | |
| 5,775,014 A | 7/1998 | Lin | |
| 5,878,515 A | 3/1999 | Yang | |
| 6,042,022 A | 3/2000 | Rogozinski et al. | |
| 6,065,640 A | 5/2000 | Ho et al. | |
| 6,171,560 B1 | 1/2001 | Pesu et al. | |
| 6,269,566 B1 | 8/2001 | Lo | |
| 6,318,010 B1 | 11/2001 | Tsai | |
| 6,345,457 B1 | 2/2002 | Bradley | |
| 6,385,880 B1 | 5/2002 | Naragon | |
| 6,449,887 B1 | 9/2002 | Song | |
| 6,508,022 B2 | 1/2003 | Huang | |
| 6,568,107 B2 * | 5/2003 | Yuen .............................. | 40/406 |
| 6,588,130 B1 | 7/2003 | Yang | |
| 6,848,206 B2 | 2/2005 | Zhao | |
| 6,854,208 B1 * | 2/2005 | Chuang et al. ................... | 43/125 |
| 6,857,929 B2 | 2/2005 | Liao et al. | |
| 6,880,274 B2 | 4/2005 | Liu | |
| 6,895,703 B2 | 5/2005 | Tien | |
| 7,065,908 B1 | 6/2006 | Pineda-Sanchez et al. | |
| 7,188,783 B2 * | 3/2007 | Ivey et al. ...................... | 239/136 |
| 2002/0184801 A1 | 12/2002 | Naragon | |
| 2003/0177677 A1 | 9/2003 | Acosta, Sr. | |
| 2003/0196357 A1 * | 10/2003 | Knapp et al. .................... | 40/410 |
| 2004/0055190 A1 | 3/2004 | Liu | |
| 2004/0194819 A1 | 10/2004 | Dweck | |
| 2005/0039358 A1 | 2/2005 | Rust | |
| 2005/0285538 A1 * | 12/2005 | Jaworski et al. ................. | 315/76 |

FOREIGN PATENT DOCUMENTS

FR 2804000 A1 * 7/2001

* cited by examiner

*Primary Examiner* — Sean E Conley

(74) *Attorney, Agent, or Firm* — Fredrikson & Byron, P.A.

(57) ABSTRACT

A snowglobe assembly for emitting a fragrance to an ambient environment. A motor may be provided to agitate particulate material inside the globe.

7 Claims, 2 Drawing Sheets

FRAGRANCE EMITTING SNOW GLOBE

FIELD OF THE INVENTION

The embodiments of the invention relate to globe assemblies and, more particularly, to globe assemblies that emit a fragrance.

BACKGROUND

The use of globe assemblies is known in the prior art. Many known systems have particulate material suspended in a liquid in the globe assembly and have means, such as a motor, for circulating or agitating the particulate material suspended in a liquid if the globe assembly to give the appearance of snow falling. Often there is some type of figurine located in the globe assembly. It is also known to incorporate music assemblies for generating an aural tune as well as light sources.

SUMMARY

According to one aspect of the invention, a snowglobe is provided having a base member, a globe member, a fan and a fragrance source. The base member is adapted for resting upon a horizontal support surface. It has a bottom wall and a perimeter wall extending upwardly, from the bottom wall. The base member has a substantially hollow space and an air intake port and an air outflow port. The globe member is substantially transparent and has a perimeter wall defining an interior space. The globe member is mounted on the base member. The fan is located in the hollow space wherein the fan, in operation, creates an air stream that draws exterior air to the base member through the air intake port and circulates it to the air out flow port. The fragrance source is located inside the hollow space of the base member and is positioned in the air stream created by the fan. There is at least one opening in the base member for allowing a scent generated by the fragrance source to escape the substantially hollow space of the base to an exterior of the base member.

DETAILED DESCRIPTION OF THE PREFERRED EMBODIMENTS

Figure 1:
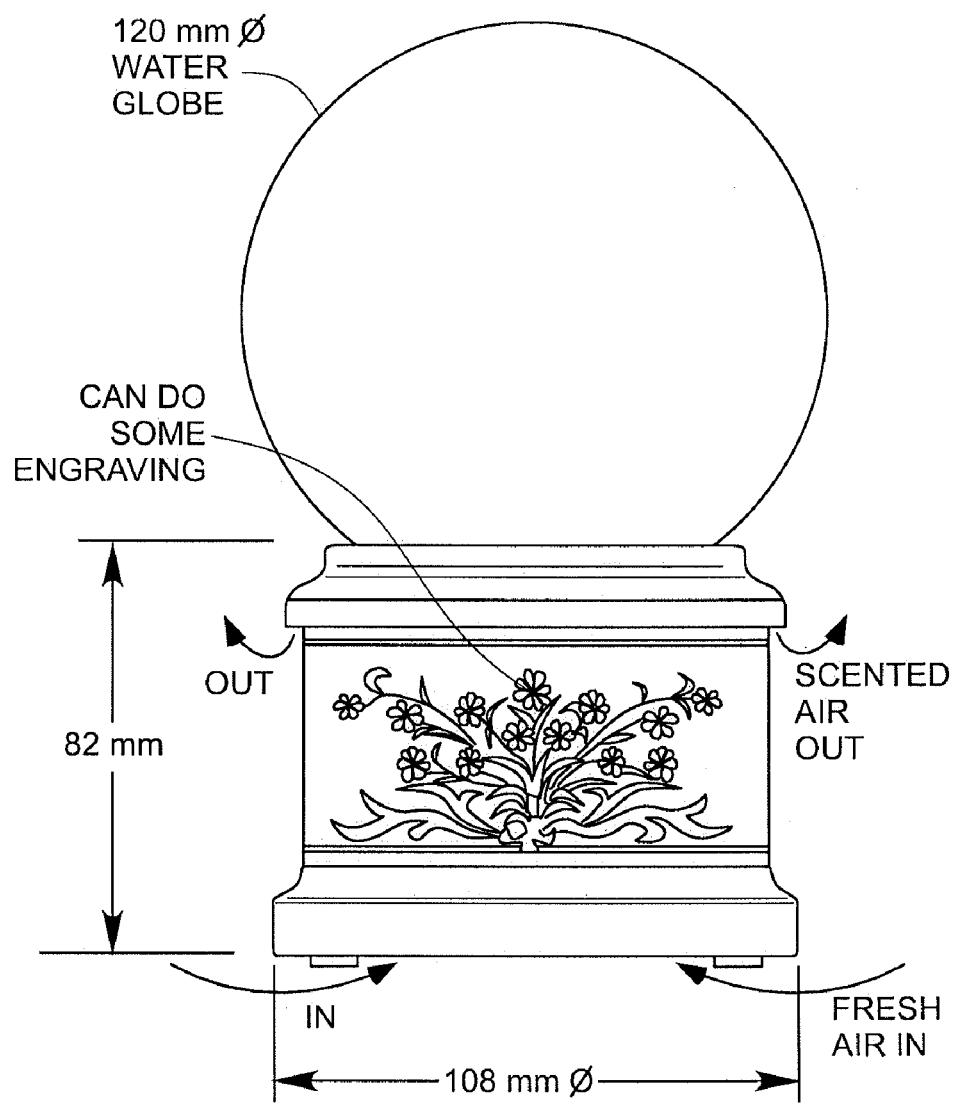
FIG. 1 is a front elevation view of a globe assembly according to embodiments of the invention.

FIG. 1 is a front elevation view of a globe assembly according to embodiments of the invention. The globe assembly 10 generally includes a base member 12 and a globe member 18. The base member 12 is adapted for resting upon a horizontal support surface such as a table. The base member 12 has a bottom wall 14 and a perimeter wall 16 that extends upwardly from the bottom wall 14. The base member 12 is substantially hollow. The globe member 18 is mounted on the base member 12. The globe member 18 has a perimeter wall 19 that defines an interior space 20. The perimeter wall 18 is substantially spherical although it may have other desired shapes. The perimeter wall 18 is also substantially transparent and is preferably substantially transparent about its entirety so as not to block viewing of the interior space 20 of objects that may be located in the interior space of the globe member 18.

The globe member 18 is substantially filled with a liquid media 22, and a quantity of particulate material 24. The particulate material 24 may be temporarily suspended in the liquid media 22 upon disturbance or movement of the liquid media. The particulate material is often shaped to resemble snow or snow flakes. The agitated particulate material relatively slowly descends through gravitational forces on the liquid media and particulate material to thereby simulate snow fall in the interior space 20 of the globe member 18.

The embodiments of the globe assembly may also include a moving means (not shown), such as motor assembly, for continuously agitating the liquid media and thus the particulate material while the motor assembly is active. This will create a continuous snowfall effect of the particulate matter as long as the motor is operating.

The moving means may include a motor assembly that is positioned in the hollow space of the base member. A rotating member (not shown) such as an impeller is operationally coupled to the motor assembly as well known to those of ordinary skill. The rotating member may be provided with blades adapted to create the agitation in the liquid media.

In one embodiment, a battery may be provided in the hollow space of the base member. The battery provides electrical energy to the motor assembly. A switch member is positioned substantially within the base member and is accessible to a user through a switch aperture n the base member. The switch member is operationally coupled to the battery member and the motor assembly. The switch member has a first position that permits electrical energy to flow from the battery to the motor assembly. The switch member has a second position that inhibits electrical energy flowing from the battery to the motor assembly.

In another embodiment, an electrical input connector may be used instead of, or in addition to, the battery to operatively couple the motor assembly to a power outlet, such as a wall socket. The electrical input connector 50 is preferably coupled to the base member. The electrical input connector 50 facilitates supply of energy to the motor assembly. A cord assembly 52 is designed to be coupled to a conventional household electrical outlet and the electrical input connector 50. The cord assembly 52 may also include an AC adapter, if necessary.

A music assembly may be provided and located substantially within the base member 12. In such a case, the base member 12 would be provided with a plurality of music apertures to allow music to be heard externally of the base member. The music assembly may be controlled by the same switch controlling the motor assembly, or a separate switch may be provided so that it operates independently from the motor assembly.

Located within the globe assembly may be a figurine. The figurine may be of a person or persons, or of an object or a plurality of objects, for example, a small village. The figurine may be stationary or it may rotate. In particular, the figurine may be operatively coupled to the motor assembly, as would be well known to those of ordinary skill in the art to rotate with the motor assembly.

Figure 2:
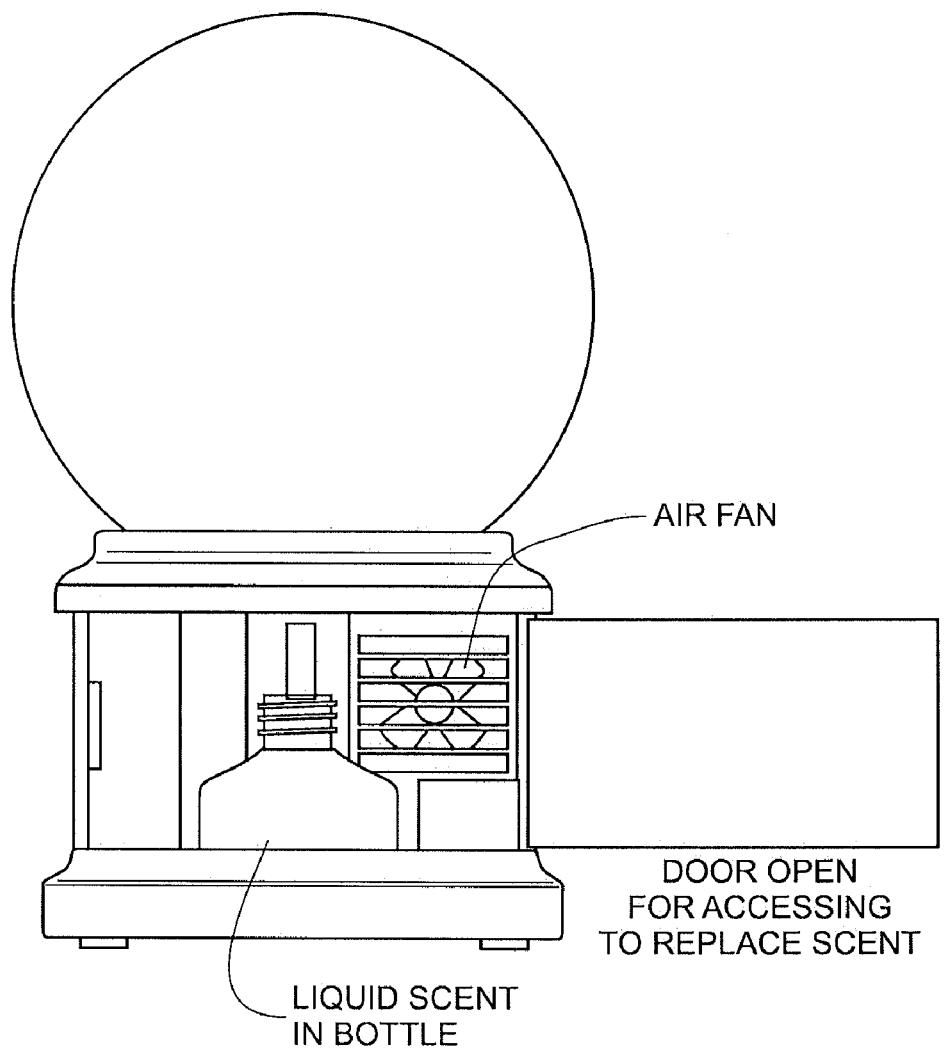
FIG. 2 is the globe assembly shown in FIG. 1 with a door located on the base member opened to expose a portion of a substantially hollow interior of the base member.

FIG. 2 is the globe assembly shown in FIG. 1 with a door forming part of the perimeter wall of the base member opened to expose a portion of a substantially hollow interior of the base member. Located within the substantially hollow space of the base member is a fragrance source as well as a fan. The fragrance source may take many forms. For example, it may be a solid gel such as those seen in air fresheners, or fragrance impregnated pellets. Alternatively, it may be a volatile fluid in which case preferably a wick is provided and partially immersed in the fluid.

Wick in one example is formed from a plastic material such as nylon, or in particular ultra high molecular weight, high density polyethylene (HDPE). Alternatively, wick could be formed from another material (e.g., cotton, fiber, capillary, stone, ceramic, etc.). Fragrance source, in one example, is a liquid dispenser that is designed to disseminate a volatile liquid, such as a fragrance compound, into a room. The fragrance compound emanates from the wick at room ambient temperature and is moved into the ambient air via a generated air stream as will be described below.

The wick and fragrance source can release a fragrance in a variety of ways. For example, wick and fragrance source could be episodic, meaning that a fragrance is only released for a short period of time, such as a few hours or even minutes. Alternatively, the wick and fragrance source could release a fragrance for longer periods of time, such as days, weeks, or months. The longevity of wick and/or fragrance source will depend on the needs of the designers, manufacturers, buyers, and consumers. It should also be noted that wick and fragrance source could be replaced by another device that emanates a fragrance (e.g., gels, solids, fogs, aerosols, etc.), as long as the device that produces the fragrance is positioned such that the fragrance is placed in the air stream.

As shown in FIG. 2, in this embodiment, the fragrance source takes the form of a liquid housed in a container having a wick partially submerged in the liquid. Preferably, a fan is located in the substantially hollow space of the base to create an air current. The air current it generates will be directed against the exposed wick to help disperse the fragrance. The base member has perforations or apertures formed in its bottom wall (not shown) that allow fresh air into the substantially hollow space of the base. Located at the top of the base member are perforations or apertures that allow the scented air to escape into the ambient air outside of the base member. The fan assembly may generate the air stream and may be controlled by the same switch controlling the motor assembly, or a separate switch may provided so that it operates independently from the motor assembly.

The base member is provided with a door in its perimeter wall that can be opened to partially expose the substantially hollow space. A user can thus access the compartment that holds the battery so that it can be easily replaced. Also, the container housing the fragrance can be refilled with the same scent or a different one depending on the users preference. Also, the fan assembly can be accessed in case it needs servicing.

In use, a user can shake the globe and base assembly if it is not provided with a motor to agitate the snow or, alternatively, the user turns on the motor assembly. The air fan may be activated so that a fragrance is emitted by the base member into the atmosphere and enjoyed by the user. For example, if a figurine is provided in the globe member, the user may fill the liquid container with an appropriate fragrance. For example, if a Christmas holiday type figurine is in the globe's interior, the user may select an appropriate fragrance such as pine tree or bay berry. If the figuring is a Fall or Halloween type figuring, the user may select a fragrance such as pumpkin. The same can be said for the various seasons and holidays.

The exterior of the base member's perimeter wall may be decorated as well perhaps with some engravings as shown in FIG. 1, or a picture, for example.

What is claimed is:

1. A snow globe assembly comprising:
   a base member adapted for resting upon a horizontal support surface, said base member having a bottom wall, said base member having a perimeter wall extending upwardly from said bottom wall, said base member having substantially hollow space, the base member having an air intake port and an air outflow port;
   a globe member being substantially transparent, said globe member having a perimeter wall defining an interior space, said globe member being mounted on said base member;
   a fan located within said hollow space wherein the fan, in operation, creates an air stream that draws exterior air to the base member through the air intake port and circulates it to the air outflow port;
   a fragrance source located inside the substantially hollow space of said base member and positioned in the air stream created by the fan, wherein the fragrance source is a replaceable liquid dispenser that disseminates a volatile liquid;
   at least one opening in said base member for allowing a scent generated by the fragrance source to escape the substantially hollow space of said base to an exterior of said base member;
   a door located on said base member for providing access to the fragrance source in the substantially hollow space of said base member; and
   a liquid medium positioned in said interior space of said globe member, said interior space of said globe member being substantially filled with said liquid medium; and
   a quantity of particulate material in said liquid medium, said particulate material being temporarily suspended in said liquid media for simulating snow fall within the globe member.

2. The assembly of claim 1 further comprising:
   moving means for moving said liquid media inside the globe member in a manner to create the look of falling snow.

3. The assembly of claim 2 wherein said moving means comprises a motor assembly positioned in said base member, and a rotating member for creating turbulence in said liquid media, said rotational member being operatively coupled to the motor assembly.

4. The assembly of claim 1 further comprising a music assembly for providing a melodic aural signal during operation of said music assembly.

5. The assembly of claim 3 further comprising:
   a battery for providing electrical energy for said motor assembly, said battery being positioned in said base member and a switch being operationally coupled between the battery and the motor assembly, said switch member having a first position permitting electrical energy to flow from said battery to sad motor assembly and said switch having a second position inhibiting electrical energy to flow to said motor assembly from said battery.

6. The assembly according to claim 3 further comprising:
   an electrical input connector operationally coupled to said motor assembly, said electrical input connector facilitating supply of electrical energy to said motor assembly; and
   a cord assembly adapted for coupling to an electrical input connector, said cord assembly facilitating supply of electrical current from an outlet to said electrical input connector.

7. The assembly according to claim 1 further comprising a figurine located in the interior space of said globe.

* * * * *